United States Patent
White et al.

(10) Patent No.: US 9,629,580 B2
(45) Date of Patent: Apr. 25, 2017

(54) SYSTEM AND METHOD FOR LIGAMENT INSERTION IN KNEE JOINT SURGERIES USING ADAPTIVE MIGRATION OF LIGAMENT INSERTION GEOMETRY

(71) Applicants: Bruce F. White, Boston, MA (US); Darryl D'Lima, San Diego, MA (US)

(72) Inventors: Bruce F. White, Boston, MA (US); Darryl D'Lima, San Diego, MA (US)

(73) Assignee: Advanced Mechanical Technology, Inc., Watertown, MA (US)

( * ) Notice: Subject to any disclaimer, the term of this patent is extended or adjusted under 35 U.S.C. 154(b) by 35 days.

(21) Appl. No.: 14/661,190

(22) Filed: Mar. 18, 2015

(65) Prior Publication Data

US 2015/0265363 A1    Sep. 24, 2015

Related U.S. Application Data

(60) Provisional application No. 61/955,446, filed on Mar. 19, 2014.

(51) Int. Cl.
*A61B 5/103* (2006.01)
*A61B 5/00* (2006.01)
(Continued)

(52) U.S. Cl.
CPC .......... *A61B 5/4533* (2013.01); *A61B 5/1121* (2013.01); *A61B 5/4528* (2013.01);
(Continued)

(58) Field of Classification Search
CPC ............ A61B 17/1714; A61B 17/1764; A61B 2034/105; A61B 2034/107;
(Continued)

(56) References Cited

U.S. PATENT DOCUMENTS 5,014,719 A    5/1991  McLeod
6,161,080 A   12/2000  Aouni-Ateshian et al.
(Continued)

FOREIGN PATENT DOCUMENTS

WO    2010131121 A1    11/2010

OTHER PUBLICATIONS

B.M. Boszczyk et al., "A Geometrical Model of Vertical Translation and Alar Ligament Tension in Atlanto-Axial Rotation," European Spine Journal, Mar. 2, 2012, pp. 1575-1579, vol. 21 Issue 8, Springer.
(Continued)

*Primary Examiner* — Anu Ramana
*Assistant Examiner* — Jessica Weiss
(74) *Attorney, Agent, or Firm* — AKC Patents, LLC; Aliki K. Collins (57) ABSTRACT

A system for providing feedback during ligament insertion in knee joint orthopedic surgeries includes an imaging device providing knee joint articular surface geometry data, a position measuring device providing distal ligament insertion sites, a strain measuring device providing ligament reference strain, a drive system providing a prescribed kinematic path for the knee joint and an adaptive migration application. The adaptive migration application receives inputs including the knee joint articular surface geometry data, the distal ligament insertion sites, the ligament reference strain and the prescribed kinematic path for the knee joint and generates outputs including sets of isotonic, hypertonic and hypotonic points representing proximal insertion sites of ligament fiber associated with prescribed distal ligament insertion sites.

9 Claims, 11 Drawing Sheets

(51) Int. Cl.
*A61B 5/11* (2006.01)
*A61B 34/10* (2016.01)
*A61B 17/17* (2006.01)

(52) U.S. Cl.
CPC ............ *A61B 5/4585* (2013.01); *A61B 34/10* (2016.02); *A61B 17/1714* (2013.01); *A61B 17/1764* (2013.01); *A61B 2034/105* (2016.02); *A61B 2034/107* (2016.02); *A61B 2505/05* (2013.01)

(58) Field of Classification Search
CPC ... A61B 2505/05; A61B 34/10; A61B 5/1121; A61B 5/4528; A61B 5/4533; A61B 5/4585; A61B 5/064; A61B 19/5244
USPC ................................ 600/587, 595; 606/102
See application file for complete search history.

(56) References Cited

U.S. PATENT DOCUMENTS

| | | | |
|---|---|---|---|
| 7,575,602 | B2 | 8/2009 | Amirouche et al. |
| 7,643,868 | B2 | 1/2010 | Giordano et al. |
| 7,823,460 | B2 | 11/2010 | White |
| 8,211,041 | B2 | 7/2012 | Fisher et al. |
| 8,805,662 | B2 | 8/2014 | White |
| 2003/0153978 | A1 | 8/2003 | Whiteside |
| 2004/0254771 | A1 | 12/2004 | Riener et al. |
| 2005/0119661 | A1 | 6/2005 | Hodgson et al. |
| 2006/0161052 | A1* | 7/2006 | Colombet .............. A61B 5/064 600/300 |
| 2010/0010506 | A1 | 1/2010 | Murphy |
| 2010/0234770 | A1 | 9/2010 | Colombet et al. |
| 2010/0298894 | A1 | 11/2010 | Bojarski et al. |
| 2011/0029093 | A1 | 2/2011 | Bojarski et al. |
| 2011/0118878 | A1 | 5/2011 | White |
| 2013/0041289 | A1 | 2/2013 | Sena et al. |
| 2013/0317511 | A1 | 11/2013 | Bojarski et al. |
| 2014/0039631 | A1 | 2/2014 | Bojarski et al. |

OTHER PUBLICATIONS

Robert F. Laprade et al., "The Anatomy of the Medial Part of the Knee," The Journal of Bone & Joint Surgery, Sep. 26, 2007, pp. 2000-2010, vol. 89-A No. 9, The Journal of Bone and Joint Surgery Inc., Needham MA.

V.Pniskerova et al., "Tibiofemoral movement 1", The Journal of Bone & Joint Surgery, Nov. 2000, vol. 82-B, No. 8, p. 1189, The Journal of Bone and Joint Surgery Inc., Needham MA.

Thomopoulos et al., "The development and morphogenesis of the tendon-to-bone insertion", J. Muskoloskelet Neuronal Interact, Mar. 2010; 10(1):35-45.

Wei et al., "The postnatal development of the insertions of the medial collateral ligament", Anat Embryol (Berl) Jan. 1996; 193(1):53-59.

Doerfl, J, "Migration of tendinous insertions" Journal of Anatomy 131(1):179-195 1980.

Wang et al., "The remarkable migration of the medial collateral ligament" J. Anat., Apr. 2014; 224(4):490-8.

* cited by examiner

SYSTEM AND METHOD FOR LIGAMENT INSERTION IN KNEE JOINT SURGERIES USING ADAPTIVE MIGRATION OF LIGAMENT INSERTION GEOMETRY

CROSS REFERENCE TO RELATED CO-PENDING APPLICATIONS

This application claims the benefit of U.S. provisional application Ser. No. 61/955,446 filed Mar. 19, 2014 and entitled "SYSTEM AND METHOD FOR KNEE JOINT SIMULATION USING ADAPTIVE MIGRATION OF LIGAMENT INSERTION GEOMETRY", the contents of which are expressly incorporated herein by reference.

FIELD OF THE INVENTION

The present invention relates to a system and a method for ligament insertion in knee joint surgeries, and more particularly to ligament insertion in knee joint surgeries that uses adaptive migration of ligament insertion geometry.

BACKGROUND OF THE INVENTION

Figure 11:
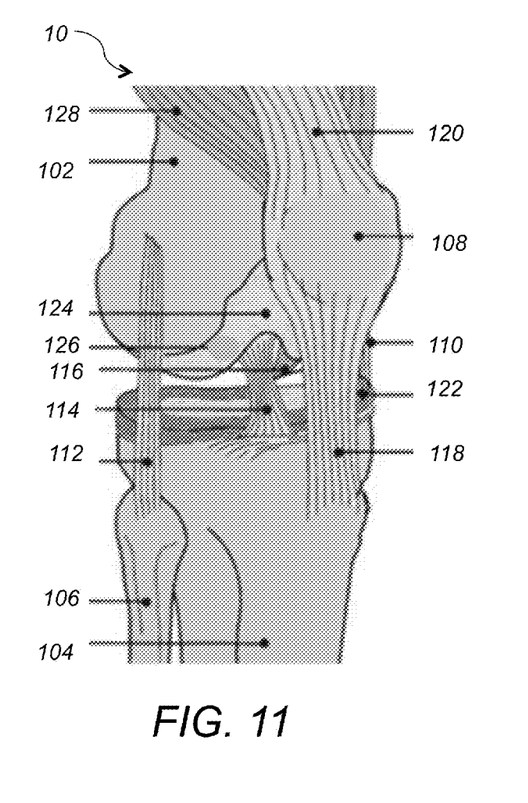
FIG. 11 is a schematic diagram of the knee anatomy.

The knee joint is one of the most important and strongest joints in the human body. It is designed to support the weight of a person's body and to provide articulating motion between the upper leg and the lower leg. Referring to FIG. 11, human knee joint 10 provides a hinged connection between the femur bone 102 of the upper leg and the tibia 104 and fibular 106 bones of the lower leg. The bone anatomy of the knee joint also includes the patella bone 108 located in the center of the knee. The distal end of the femur bone 102 includes two convex epicondyles, i.e., lateral epicondyle 126 and medial epicondyle 127 that interface and articulate with two corresponding condyles formed at the proximal end of the tibia bone 104, i.e., lateral condyle and medial condyle, respectively. The end surfaces of the condyles and epicondyles are covered by the articular cartilage 124 and between the femur and the tibia there is a plate of cartilage known as the meniscus 122. The knee joint bones are held together by a series of ligaments including the medial collateral ligament (MCL) 110, the lateral collateral ligament (LCL) 112, the anterior cruciate ligament (ACL) 114, the posterior cruciate ligament (PCL) 116, the patella tendon 118 and the quadriceps tendon 120. The MCL connects the medial site of the femur to the tibia. The LCL connects the lateral site of the femur to the fibula. The ACL extends obliquely from and connects the inner surface of the lateral epicondyle of the femur to the anterior condyle of the tibia. The PCL extends obliquely from and connects the inner surface of the medial epicondyle of the femur to the posterior condyle of the tibia. The patella bone is held in place in the anterior surface of the knee by the patellar tendon and the quadriceps tendon. The overall range of motion of the knee depends upon the specific anatomy of the bones and the ligaments and in general it allows about 120° degrees of flexion motion. In addition to the knee bones and ligaments, there is a joint capsule and small pockets of synovial fluids (i.e., bursae) that surround the knee and provide strength and lubrication. The ligaments and the fluid capsule and bursae are referred to as the soft tissue of the knee joint.

The specific anatomy of the knee bones and ligaments evolves and develops during maturation of animals and humans. Ligament migration under the evolving demands of loading and weight bearing during early stages of development has been reported by numerous researchers. Wei et al., in a study analyzing the morphological changes and insertion migration in medial collateral ligaments (MCL) states: "during development, the MCL maintains its relative position to the knee joint system despite growth at the tibial epiphyses." Wei et al., goes on to say: "it may be speculated that increased mechanical loading on the periosteum mediated by the attaching ligament may stimulate periosteal cells to differentiate into osteoclasts by mechanisms mentioned above." Dörfl informs us that: "If bone is inspected at different ages, one sees that the insertions of muscles and ligaments on the diaphysis occupy the same relative positions with respect to the extremities of the bone. This observation can only be explained by the migration of the insertions on the diaphysis, for it is known that there is no interstitial growth of the diaphysis." Thomopoulos et al., describes the morphogenesis of tendon to bone insertion and identifies several mechanobiological mechanisms and factors which mitigate ligament insertion site development and migration. Wang et al., states: "The most curious of the migratory sites is the MCL, as it is an inelastic fibrous ligament that during linear growth seems to be under heavy and continuous tension from its origin on the distal femur yet manages to migrate away from rather than toward the direction of the applied load."

It is clear that during the developmental phase, the ligament structure adapts to the developing bony structure and perhaps the osseous structures adapt and are shaped by the developing ligament structure as a result of the imposed mechanical loading. This synergistic growth process maintains the needed joint mobility while providing the requisite joint stability necessary for a functional knee system throughout the development phase and into maturity.

An anatomical and functional knowledge of ligament insertion sites is necessary to the understanding of the mechanics of the knee. Much recent research focuses on accurate anatomical studies necessary to help guide the surgeon in ligament reconstructive surgery and total knee replacement. Many of these studies focus on quantification of the ligament insertion site geometry and neighboring osseous landmarks. These studies are undoubtedly excellent references for surgeons attempting to navigate in the obscure surgical environment. However, most of these studies, even the most quantitative, omit description of the mechanical context which might be provided by measurement of the geometry of the articular surfaces. Typically we find detailed anatomical descriptions of the ligament insertion sites, accompanied by reference measurements to proximate osseous landmarks. Most frequently the osseous landmarks are of surgical interest because they are palpable or possibly visible in the near vicinity of the ligament structure of interest. But generally these landmarks are not mechanical, or if they are, their function is secondary to the principle function of the joint or perhaps structural in nature. The shape of the contiguous articular surfaces constitutes a constraint system which guides or constrains the permissible kinematics of the joint (assuming no interpenetration which is not strictly true under load). The articular contact geometry, coupled with the geometry of the ligament structure, functions synergistically to realize the requisite stability and conversely, mobility of the joint. Thus to remove description of the ligaments from the context of description of the articular surfaces provides a mechanically incomplete description of the joint.

In total knee arthroplasty (TKA) and in knee ligament reconstruction surgery, accurate positioning of the implants and accurate ligament attachment are crucial to the success of the operations. A large percentage of these operations fail and need to be repeated because it is difficult to determine the accurate positioning of the implant and the accurate ligament attachment from purely anatomical data.

One system for obtaining data indicative of a location of a ligament graft placement in ligament reconstruction surgery is described in US published application US 20100234770. This prior art system includes a position determining device that is capable of tracking relative movement of two bones using reference bodies that are attached to the bones and a pointer that has a tip for contacting a surface of at least one of the two bones in order to capture one or more reference points. The system also includes a computer that is configured to determine and track intraoperative positions of the reference bodies and the pointer and to provide isometric and impingement data for the ligament graft placement based on realistic simulation of a trajectory of a deformable ligament graft. The system generates and compares preoperative and postoperative plots that represent knee laxity as a function of flexion. However, in many cases the preoperative state of the knee and the surrounding soft tissue is already compromised and therefore trying to replicate the preoperative state of the knee joint may be not desirable.

Accordingly, there is a need for a method for simulating ligament insertion and attachment in knee surgeries that provides accurate ligament insertion and attachment without relying in the preoperative state of the knee joint.

SUMMARY OF THE INVENTION

The present invention relates to a system and a method for knee bone joint and soft tissue simulation during ligament insertion in knee joint surgeries, and more particularly to knee bone joint and soft tissue simulation that uses adaptive migration of ligament insertion geometry.

In general, in one aspect, the invention features a system for providing feedback during ligament insertion in knee joint orthopedic surgeries including an imaging device, a position measuring device, a strain measuring device, a drive system and an adaptive migration application. The imaging device provides knee joint articular surface geometry data. The position measuring device provides distal ligament insertion sites. The strain measuring device provides ligament reference strain. The drive system provides a prescribed kinematic path for the knee joint. The adaptive migration application is configured to receive inputs comprising the knee joint articular surface geometry data, the distal ligament insertion sites, the ligament reference strain and the prescribed kinematic path for the knee joint and to generate outputs comprising sets of isotonic, hypertonic and hypotonic points representing proximal insertion sites of ligament fiber associated with prescribed distal ligament insertion sites.

Implementations of this aspect of the invention may include one or more of the following features. The knee joint articular surface geometry data are represented as two tangentially intersecting circular arcs. The adaptive migration application generates the set of isotonic, hypertonic and hypotonic points by iteratively adapting the distal ligament insertion sites based on an integral of a ligament tension vector over a flexion arc. The integral of the ligament tension vector trends towards a limit of zero with successive iterations of the adaptive migration application and at the limit a distal ligament insertion site is determined that balances tensile and compressive strain over the flexion arc. A ligament stretched between two isotonic points has equal tension throughout the flexion arc. The prescribed kinematic path for the knee joint includes passive kinematics of the knee joint through a flexion arc. The prescribed kinematic path for the knee joint includes flexion, internal rotation, anterior posterior displacement or medial lateral displacement. The prescribed kinematic path for the knee joint is applied while the knee joint is constrained in two degrees of freedom. A cost function is defined based on applied strain magnitude and direction of a strain induced tension in each ligament is determined. The distal ligament insertion sites are migrated in a direction counterpoised to a line of action of the induced tension in each ligament throughout a flexion arc.

In general, in another aspect, the invention features a method for providing feedback during ligament insertion in knee joint orthopedic surgeries. Including the following: Providing an imaging device providing knee joint articular surface geometry data. Next, providing a position measuring device providing distal ligament insertion sites. Next, providing a strain measuring device providing ligament reference strain. Next, providing a drive system providing a prescribed kinematic path for the knee joint. Next, providing an adaptive migration application configured to receive inputs comprising the knee joint articular surface geometry data, the distal ligament insertion sites, the ligament reference strain and the prescribed kinematic path for the knee joint and to generate outputs comprising sets of isotonic, hypertonic and hypotonic points representing proximal insertion sites of ligament fiber associated with prescribed distal ligament insertion sites.

The details of one or more embodiments of the invention are set forth in the accompanying drawings and description below. Other features, objects, and advantages of the invention will be apparent from the following description of the preferred embodiments, the drawings, and the claims.

BRIEF DESCRIPTION OF THE DRAWINGS

Referring to the figures, wherein like numerals represent like parts throughout the several views.

DETAILED DESCRIPTION OF THE INVENTION

In ligament reconstruction surgeries, surgeons try to determine and locate tibia and femur points that would produce optimal isometry. Isometry exist when the distance between two points in the original configuration is the same as the distance between their corresponding images in the transformed configuration. In ligament reconstruction surgery, isometry involves replacing a resected ligament with a replacement ligament so that no length change occurs through a normal unrestricted motion arc. In general, the assumption is that it is desirable to maximized isometry in ligament reconstruction surgeries. However, this method does not always lead to successful ligament reconstruction because the initial configuration may not be optimal and because there are not truly isometric points in the knee joints.

The present invention provides a system and a method of providing improved ligament reconstruction by utilizing an adaptive migration of ligament insertion geometry. The key hypotheses of the present methodology include the following:

1) Given natural passive knee motion, with contact between the tibia and femur, there exist no pairs of points on the two bodies which can be categorized as truly isometric throughout the flexion arc.
2) Given a point on one of the joint components a second point may be chosen on the adjacent component which minimizes the change in separation distance between the two points throughout the flexion arc. Such a set of points are called "near isotonic" meaning that a fiber stretched between such points has the closest approximation of equal tension throughout the flexion arc given the constraints and geometry of contact.
3) Sets of near isotonic points may be found which, if spanned by a fiber, have on the average over the flexion arc greater or lesser tension (hypertonic, or hypotonic, respectively) than the nominal isotonic fiber described above.
4) The insertion sites of the natural ligament fibers may be represented by a collection of isotonic, hypertonic and hypotonic points when motion is prescribed through the passive flexion arc.
5) Sets of such near isotonic, hypertonic and hypotonic points closely describe the nominal ligament insertion sites in the natural knee if the distal most point is chosen to represent a point within the distal ligament insertion footprint while the proximal point is discovered using an adaptive migration optimization approach.

The adaptive migration approach involves exercising a geometric model of a knee joint through a prescribed motion path (where flexion, internal rotation, anterior posterior displacement and medial lateral motion are prescribed) while constrained in two degrees of freedom by the geometry of contact (abduction adduction and joint compression distraction). The prescribed motion path represents the passive kinematics of the knee through the flexion arc. The normal knee flexion arc extends from 0° to 135° to 145° degrees. A cost function based on the magnitude of strain is defined and the direction of action of the strain induced tension in each element is determined at each calculation step. Ligament insertion sites are migrated in a direction counterpoised to the line of action of the ligament tension throughout the flexion arc.

This adaptive migration of the insertion sites acts such that the integral of strain over the flexion arc trends towards zero with successive iterations of the computation. In the limit an insertion site is determined which optimally balances tensile and compressive strain over the prescribed flexion arc. Element reference strain can be adjusted to produce an initially slack or initially tense element as might be required to represent the physiologically condition.

In one example, the passive motion is assumed to involve minimal strain through the flexion arc. In another example, a more complex cost function is considered which balances counterpoised fibers to balance both the forces and moments acting across the joint as a result of ligament tension. There may be exceptions to the counterpoising strain cost when the joint reaches the limits of the range of motion in situations where the ligaments play a role in limiting that motion. As will be seen later this later case is easily accommodated such as in the case of the PCL in hyperextension which requires hypertonic fibers.

Figure 1:
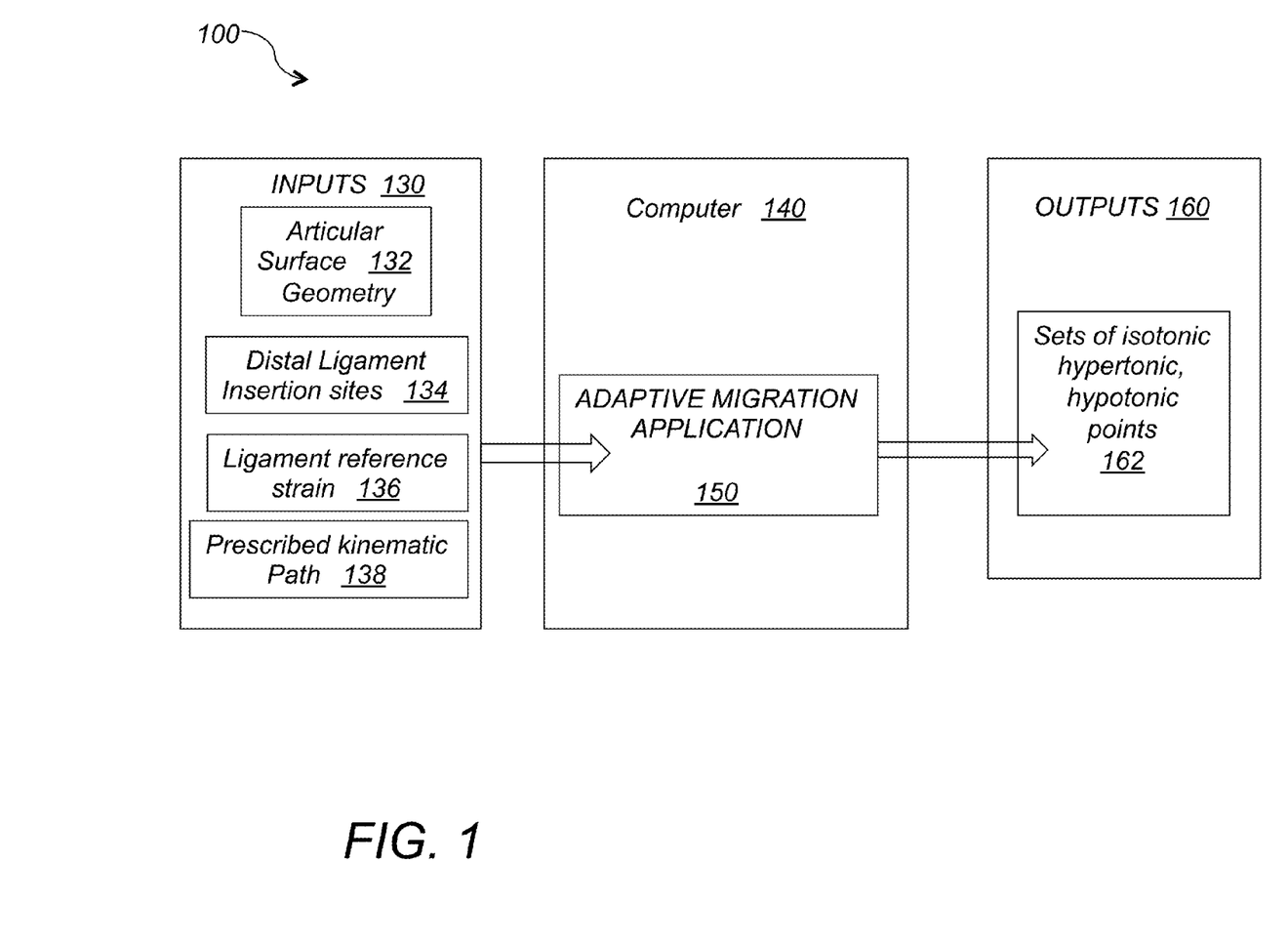
FIG. 1 is a schematic diagram of the system for ligament insertion in knee joint surgeries using an adaptive migration of ligament insertion geometry, according to this invention.

Referring to FIG. 1, the system 100 for knee joint simulation using the adaptive migration of ligament insertion geometry, according to this invention, includes a computer 140 equipped with an adaptive migration application 150, inputs 130 and outputs 160. The inputs 130 to the adaptive migration optimization include:

Articular surface geometry 132
  condylar geometry
  tibial plateau geometry
Distal ligament insertion sites 134
Ligament reference strain 136
Prescribed kinematic path 138
  Flexion arc
  Anterior posterior translation
  Internal external rotation The outputs 160 from the adaptive migration optimization include:

Sets of near isotonic, hypertonic and hypotonic points representing the proximal (femoral) insertion sites of the ligament fibers associated with the prescribed distal ligament insertion sites 162.

The knee joint articular surface geometry data is provided by an imaging device, such as X-ray, MRI, CT devices. The distal ligament insertion sites are provided by a position measuring device. The position measuring device may be an optical, acoustical, ultra-sound, video, mechanical, electromagnetic, shape recognition algorithm, or radio-frequency based emitter/detector system. In one example, the position measuring device is the Polaris system from Northern Digital Inc., Ontario, Canada. The ligament reference strain is provided by a strain measuring device, such as strain gauges, optical or magnetic devices. The prescribed kinematic path for the knee joint is provided by a drive system or a specific protocol.

In one example, the adaptive migration application 150 based on the above mentioned methodology is implemented in MATLAB™. The model is quasi three-dimensional (3D) in that independent medial and lateral condylar geometries are defined and rotations about the flexion axis, axial axis (internal external rotation) are considered. Abduction adduction and medial lateral motions are neglected in this example. Each of the condylar geometries is expressed as two tangentially intersecting circular arcs.

A simple iterative solution is developed by iteratively adapting the insertion site geometry based on the integral of the ligament tension (or compression) vector over the flexion arc. The result of the subsequent iteration is used as the insertion position for the successive iteration. When the resulting change in insertion position (calculated as the Euclidian norm of the insertion position vector) becomes sufficiently small the routine is halted. The output of the iterative calculation is an estimate of the proximal insertion site of the ligament.

Figure 1A:
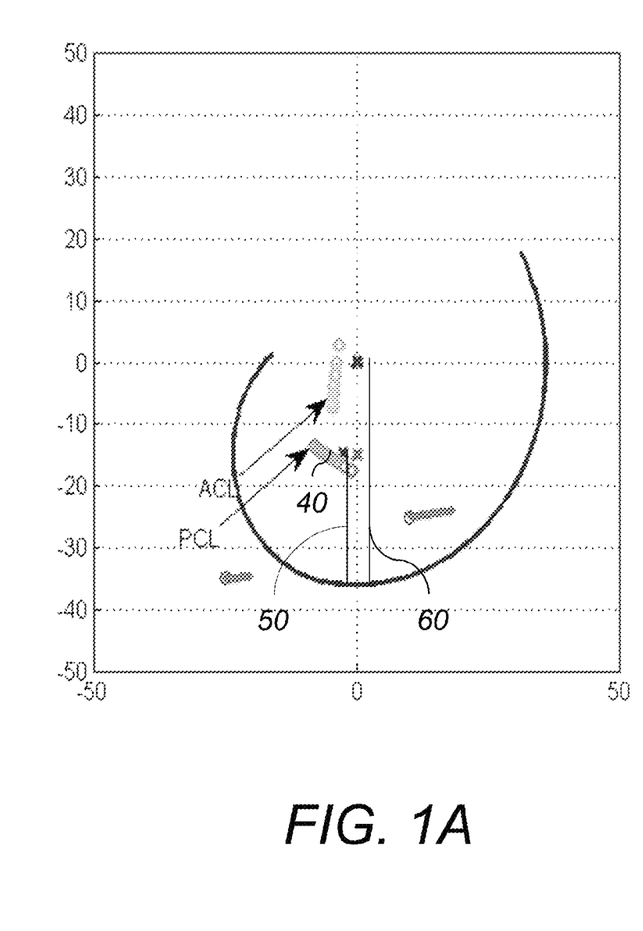
FIG. 1A shows ACL and PCL insertion sites on the femur.
Figure 1B:
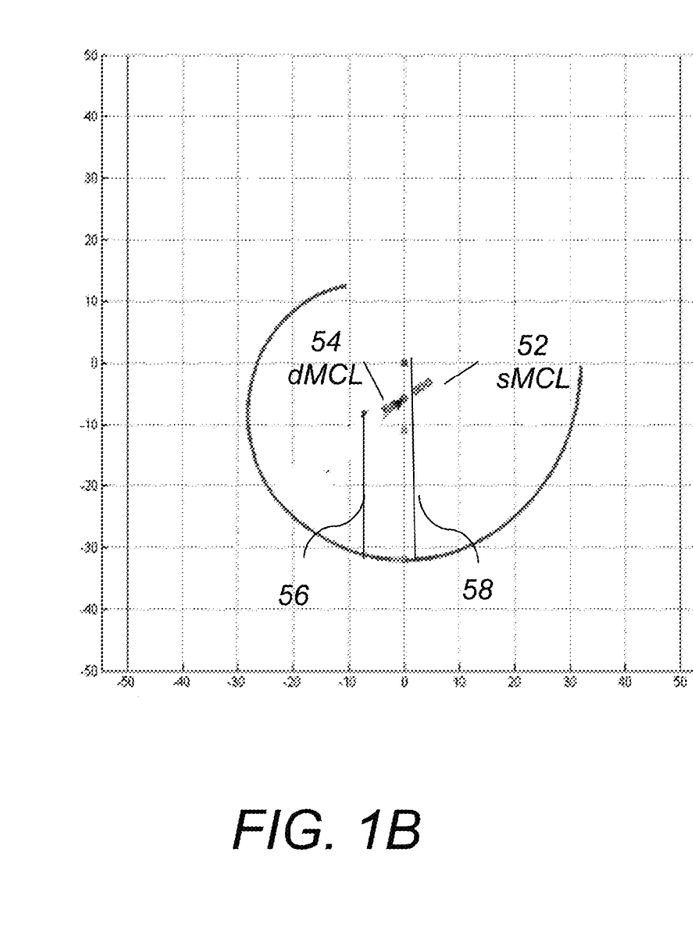
FIG. 1B shows deep MCL (dMCL) and superficial MCL (sMCL) insertion sites on the femur as determined by the adaptive migration approach.

FIG. 1A and FIG. 1B show outputs from this simulation example. FIG. 1A depicts ACL and PCL ligament insertion sites on the femur, as determined by the adaptive migration method. FIG. 1B shows deep MCL (dMCL) and superficial MCL (sMCL) ligament insertion sites on the femur, as determined by the adaptive migration method. FIG. 1A shows the lateral geometry comprised of two circles, the posterior circle with radius 50 of 21 mm and the anterior distal circle with a radius 60 of 36 mm. These are called the flexion facet (FF) and extension facet (EF) by Pinskerova. We choose the lateral geometry for the PCL despite the fact that the PCL attaches to the wall of the condylar notch of the medial condyle because the lateral geometry contributes most strongly to the known kinematics in anterior-posterior (AP) and interior-exterior (IE) through the flexion arc. Pinskerova demonstrates through a series of magnetic resonance imaging (MRI) studies in cadaveric and living subjects that the center of the posterior circle on the medial condyle moves imperceptibly through the flexion arc while the center of the posterior circle on the lateral side translates posteriorly almost 20 mm causing what is largely an internal rotation of the tibial shaft. ACL insertion sites are also shown in FIG. 1A. The relative positions of the ACL and PCL insertions are geometrically very similar to those that might be determined by drawing a line through the centroid of the corresponding natural ligament insertion footprint. Note that the series of PCL circles 40 represent a family of near isotonic insertion sites ranging from hypertonic on the left (posterior) to hypotonic on the right (anterior) for the PCL.

FIG. 1B shows the results for the superficial and deep medial collateral ligaments (sMCL and dMCL, femoralmeniscal portion). The sMCL insertions are shown as markers 52 while the dMCL are shown as markers 54. In this figure the circular geometry represents the medial geometry with a 21 mm radius posterior circle 56 and a 32 mm radius anterior distal circle 58.

Figure 2A:
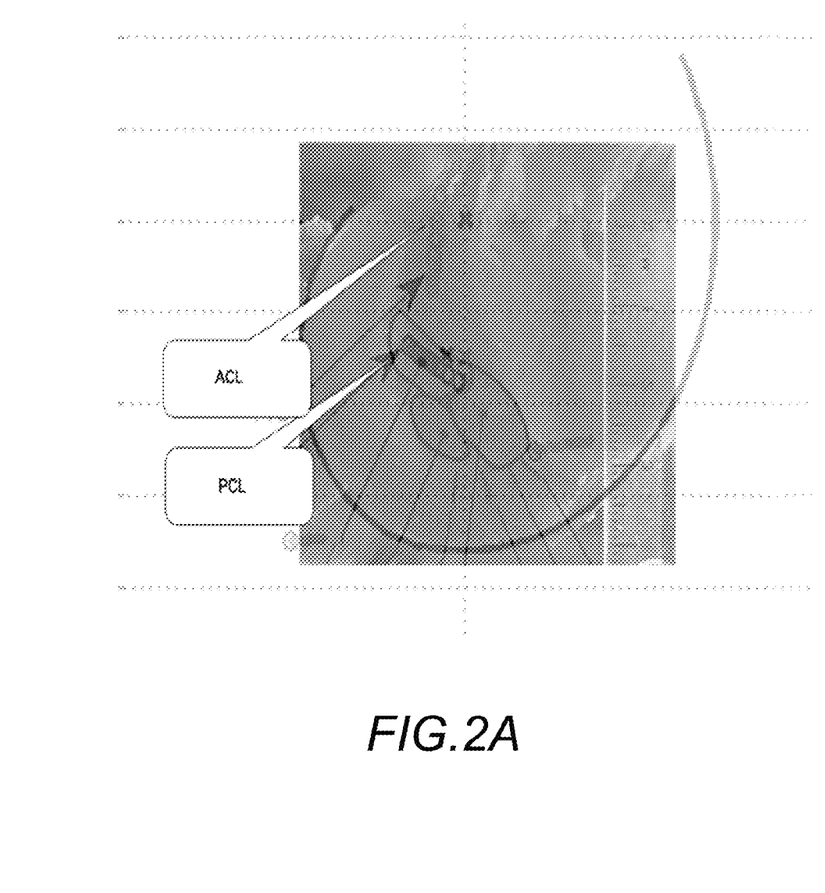
FIG. 2A and FIG. 2B show adaptive migration outputs superimposed over images of the PCL insertions and medial compartment insertions from the literature.
Figure 2B:
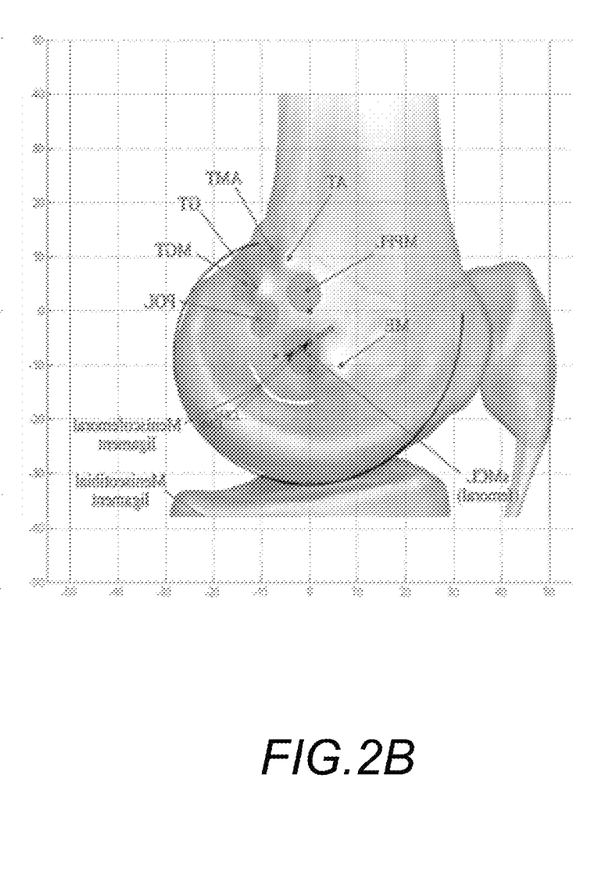

FIG. 2A and FIG. 2B depict the adaptive simulation outputs of FIG. 1A and FIG. 1 superimposed over images of the PCL insertions and medial compartment insertions, respectively. We observe a compelling similarity between the outputs of the adaptive migration approach to determining insertion geometry and insertion geometry reported in the literature. It should be noted that this visual comparison suffers many short comings. The close up photograph (attributed to Amis), shown in FIG. 2A, has potential issues of scaling and distortion due to perspective and viewing angle while the medical drawing by LaPrade, shown in FIG. 2B is not a dimensioned drawing and may reflect the artists emphasis rather than the exact positioning of insertion sites.

Figure 3A:
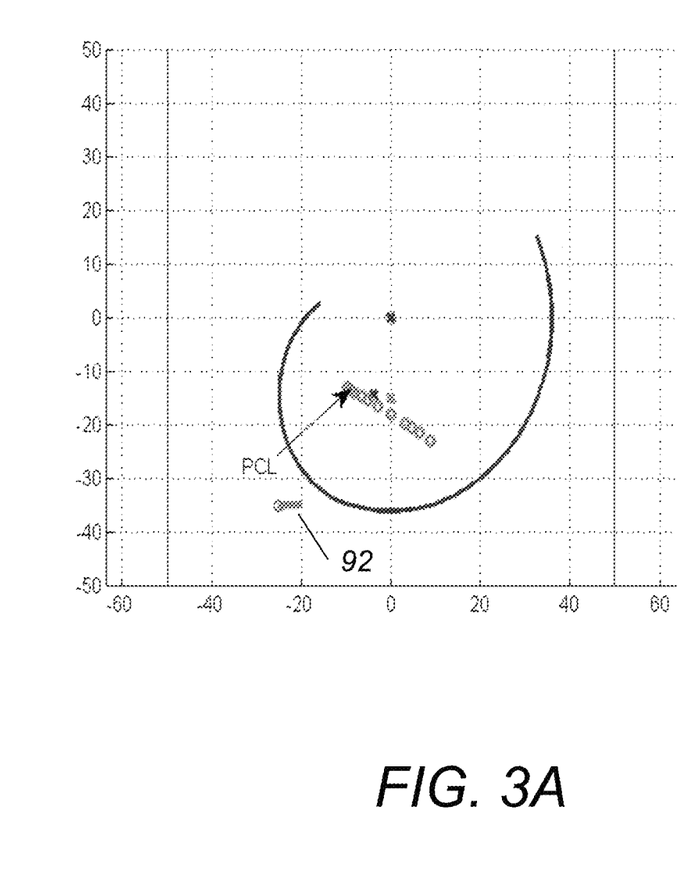
FIG. 3A shows PCL insertions extended from posterior medial bundle to anterior lateral bundle.
Figure 3B:
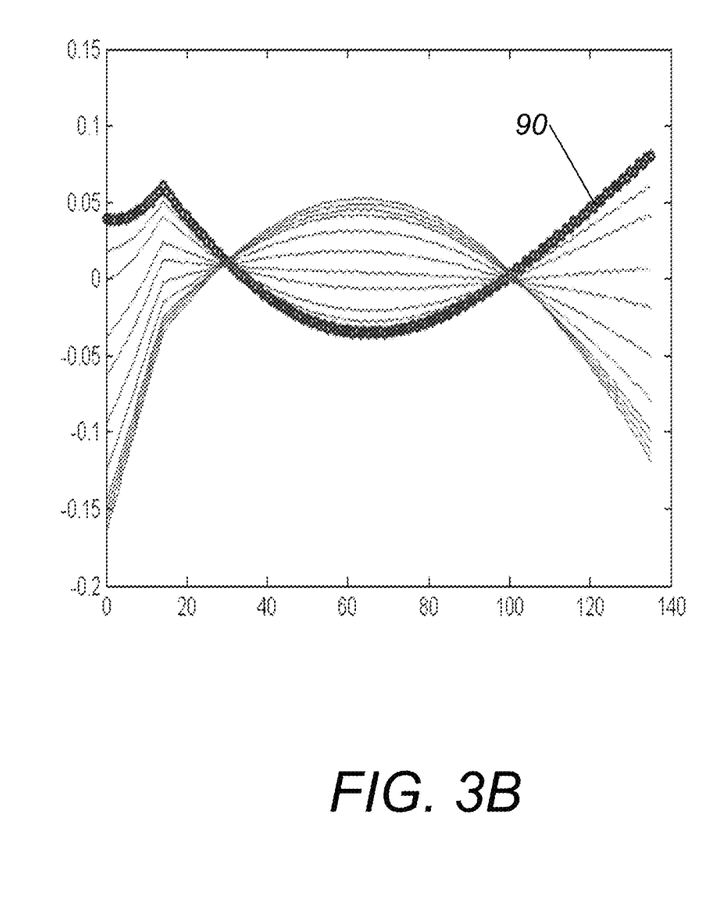
FIG. 3B shows strain in each fiber through the flexion arc (horizontal axis 0-135°)

FIG. 3A and FIG. 3B, show a series of insertion sites developed for successively decreasing initial strain. The insertion sites are organized in two groups illustrating the posterior medial bundle and the anterior lateral bundle. In particular, FIG. 3A depicts PCL insertions extended from posterior medial bundle to anterolateral bundle. FIG. 3B depicts the strain in each fiber through the flexion arc. All of the fibers originate from a single insertion site 92, shown in FIG. 3A. The horizontal axis depicts an arc from 0 to 135° degrees. Curve 90 depicts the most posterior fiber with a strain of 4% at full extension (0° degrees flexion). The strain for the most posterior fiber increases from 4% reference strain to about 6% at 15° degrees flexion arc. This point marks the transition as contact transfers from the larger diameter anterior circle (EF) to the smaller diameter posterior circle (FF). Each plot series represents a different initial reference strain. Successive fiber insertions, moving from left to right (posterior to anterior), on the plot of FIG. 3A represent insertion sites found for the conditions of diminishing reference strain. The resulting set of fibers has a recruitment sequence progressing from posterior to anterior as the knee is flexed from full extension to 135° flexion.

The following cases are offered without detailed analysis but they serve to indicate the sensitivity of the adaptive migration analysis to several different variables.

Figure 4A:
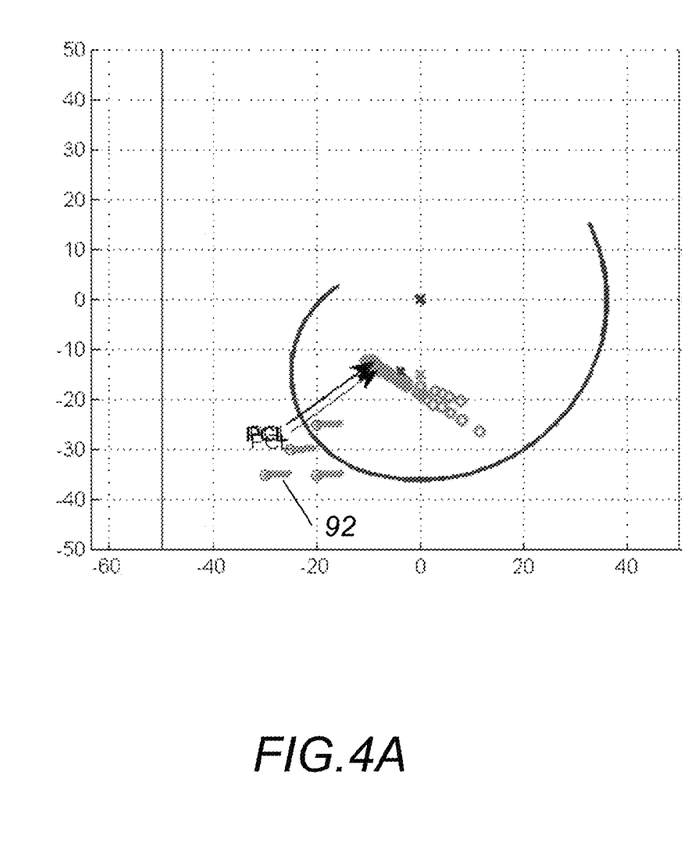
FIG. 4A shows sensitivity to tibial insertion site location.
Figure 4B:
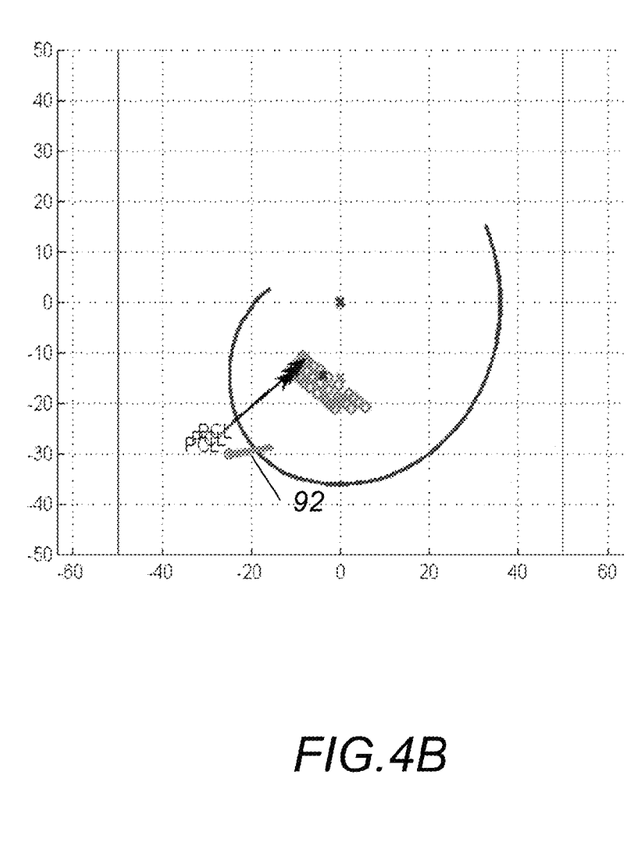
FIG. 4B shows sensitivity to lateral condylar roll back (i.e. internal rotation)

FIG. 4A depicts sensitivity to tibial insertion site locations and FIG. 4B depicts sensitivity to lateral roll back (i.e., internal rotation). FIG. 4A, shows the results of modifying the location of the distal insertion site locations 92 with chosen coordinates of (−25, −30), (−30, −35), (−20, −25), (−20, −25) mm. These locations 92 are arbitrarily chosen to cluster around the typical insertion site specified at (−25, −30). Distal insertions chosen within this 10 mm patch have relatively little influence on the resulting position of the near isotonic, hypotonic and hypertonic insertion sites found on the femur. The most notable change brought about by changing the distal insertion site is a change in slope of the isotonic line cluster. Also a notable extension of that line is seen in the case of extreme initial ligament laxity.

FIG. 4B shows three cases with different lateral 'roll back' specified at 0, 8 mm, 16 mm. The insertion sites corresponding to each roll back case lie in line clusters arranged from left to right. The resulting foot print of the insertion site cluster remains a line cluster with several parallel lines representing the several 'roll back' cases. Over the explored range the patch of insertions shows moderate sensitivity to the roll back conditions.

Figure 5A:
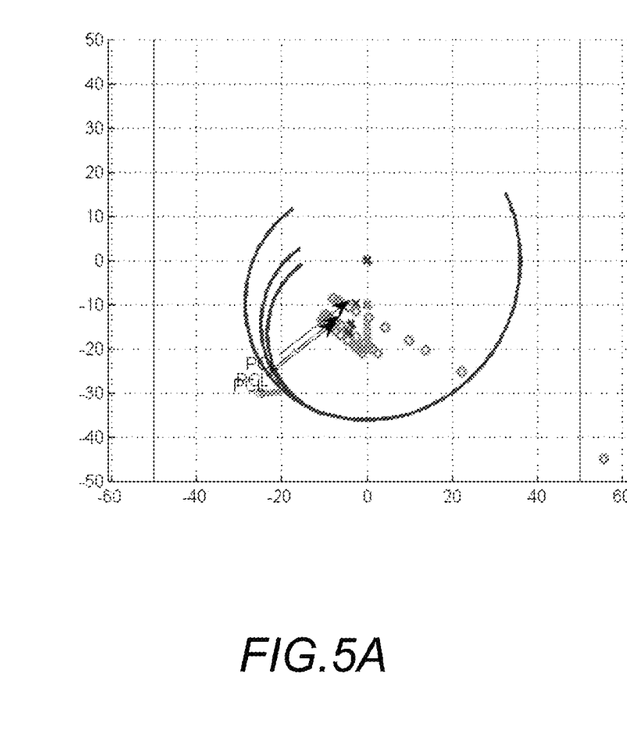
FIG. 5A shows sensitivity to posterior geometry, i.e. radius change, wherein points off the material body of the prosthesis simply indicate that the geometry will not support this extreme of hypotonic ligament condition.
Figure 5B:
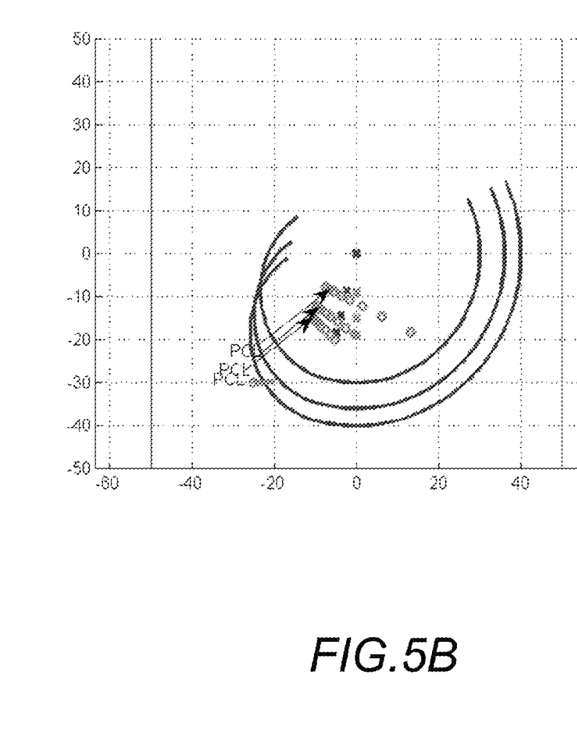
FIG. 5B shows sensitivity to anterior geometry, i.e. radius change.

FIG. 5A and FIG. 5B show the sensitivity to changes in the condyle geometry. In particular, FIG. 5A depicts sensitivity to the posterior geometry, i.e., radius change, and FIG. 5B depicts sensitivity to anterior geometry, i.e., radius change. On FIG. 5A radii of 19, 21, and 26 mm were chosen for the posterior circle (FF) while on FIG. 5B radii of 30, 36, and 40 mm were chosen for the anterior distal circle. These radii span the extremes of radius reported by Pinskerova. In terms of the overall spread of the cluster of insertions the condylar geometry seems to have considerable influence.

Figure 6A:
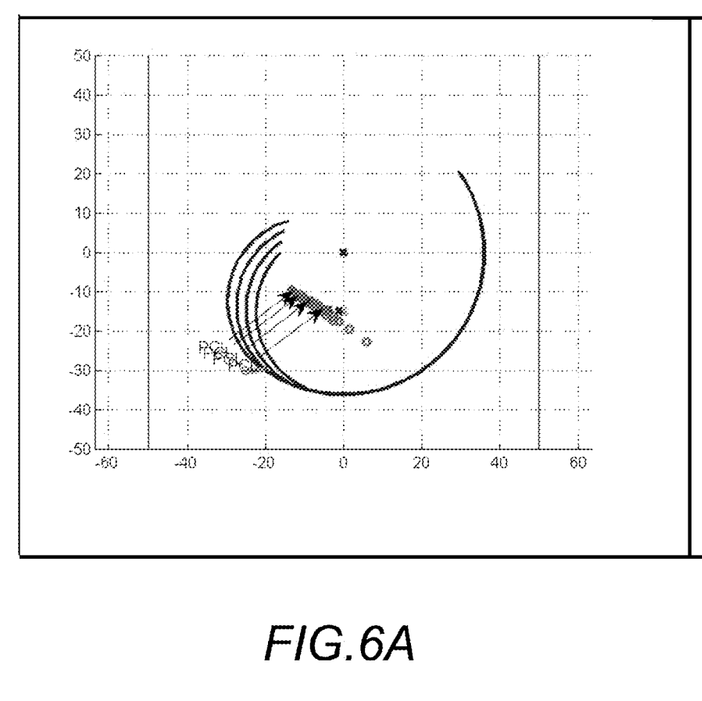
FIG. 6A shows sensitivity to change in transition angle.
Figure 6B:
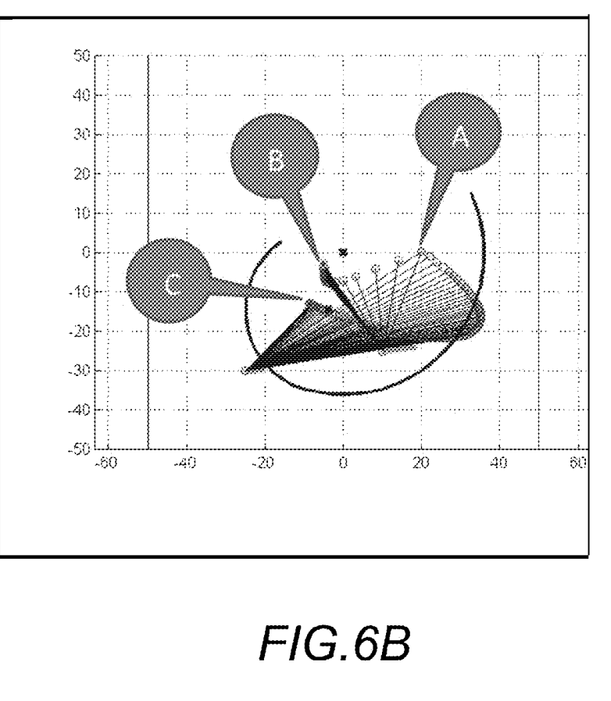
FIG. 6B shows adaptation path with ACL and PCL beginning at an arbitrary point A with convergence to final insertion points resulting in near isotonic fibers.

Another geometric feature is the transition angle specifying where the posterior circle tangentially intersects the anterior distal circle. FIG. 6A depicts the sensitivity to change in transition angle and FIG. 6B depicts adaptation path with ACL and PCL beginning at an arbitrary point A with convergence to final insertion points resulting in near isotonic fibers. FIG. 6A shows results for transition angles of 5°, 15°, 25°, 35°. Changes of this angle show very little impact on the insertion site cluster. It is possible that this variable would play a greater role if more extreme radii were used for the posterior and anterior circle geometries. FIG. 6B shows the migration of the PCL and ACL insertion sites. The initial iterates for both ACL and PCL are located at an arbitrary point A. With each iteration, the insertion site migrates toward the final near isotonic points at B and C (ACL and PCL respectively).

Figure 7:
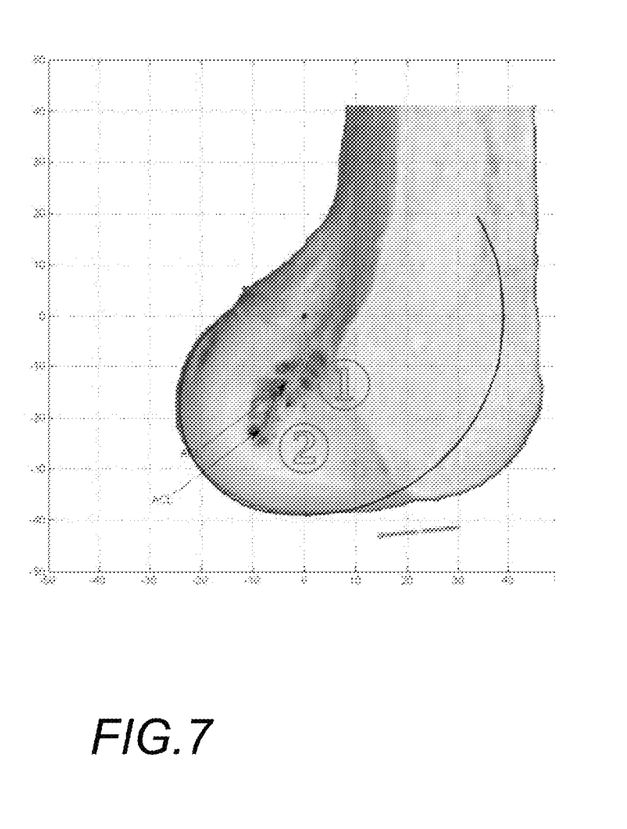
FIG. 7 shows ACL insertion sites overlaid over dissected ACL insertion foot print.

FIG. 7 depicts ACL insertion sites overlaid over dissected ACL insertion foot print. The cluster segment labeled 1 represents the discovered ligament sites for passive knee motion, and the cluster segment labeled 2 represents anteriorly loaded knee through flexion arc. The adaptive migration method has been extended to include an additional feature to determine sites which will be found under conditions of joint loading rather than under solely passive flexion. The literature indicates that we might expect a 5 to 10 mm anterior translation of the joint under loading from the quadriceps. The fibers indicated by 2 are developed by displacing the tibia anteriorly by 8 mm throughout the entire flexion arc.

Obviously ligaments are finite deformable continuous media, probably quite incompressible in nature. Clearly representation with discrete, infinitesimal non-interacting fibers is a rather crude approximation of the ligament element. Although modeling of such a structure through some manner of finite element means is intriguing it is beyond the scope of the current work. However a first order geometric model could certainly be implemented which involves wrapping fibers over known geometry. Another approach might be to provide a flexion angle based strain representing the first order effect of the geometry of windup.

As already shown, passive flexion only reveals part of the picture. Ligaments are clearly load bearing elements and as such the insertion geometry will develop to satisfy those load bearing needs. We added anterior displacement (resulting from anterior load) to the development of the ACL and the results were remarkable. Weight bearing and joint compression may play a significant role. Body weight causes one to two mm of joint compression.

Figure 8:
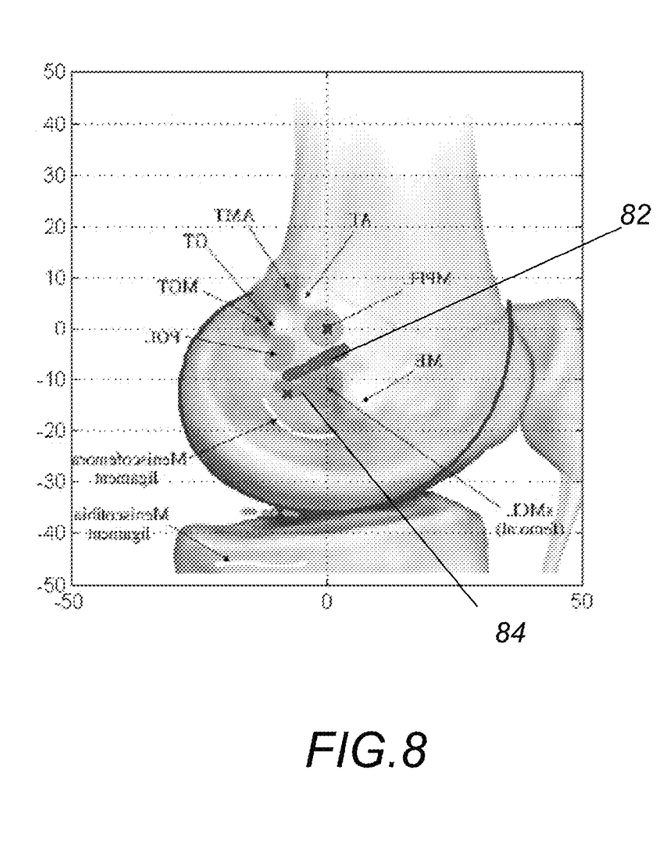
FIG. 8 shows Superficial MCL 82 and deep MCL (meniscal femoral component) 84.

The greatest bulk of the MCL sits proximal to the site adaptive migration finds. As the knee flexes the proximal anterior fibers of the MCL must wrap around the bulk of the MCL making their effective insertion closer to the lower boundary. FIG. 8 illustrates the results of inclusion of a kink model to approximate the necessity of the superficial MCL 82 to wrap around itself through the flexion arc. Item 84 depicts the deep MCL meniscal femoral component. The kink is modeled as a peg a fixed distance from the proximal insertion site about which the ligament fiber must wrap. The distance of the peg from the insertion site will be less then maximum dimension of the area of the insertion but it is not possible to formulate a better approximation without a more detailed analysis of the local material deformation.

Figure 9:
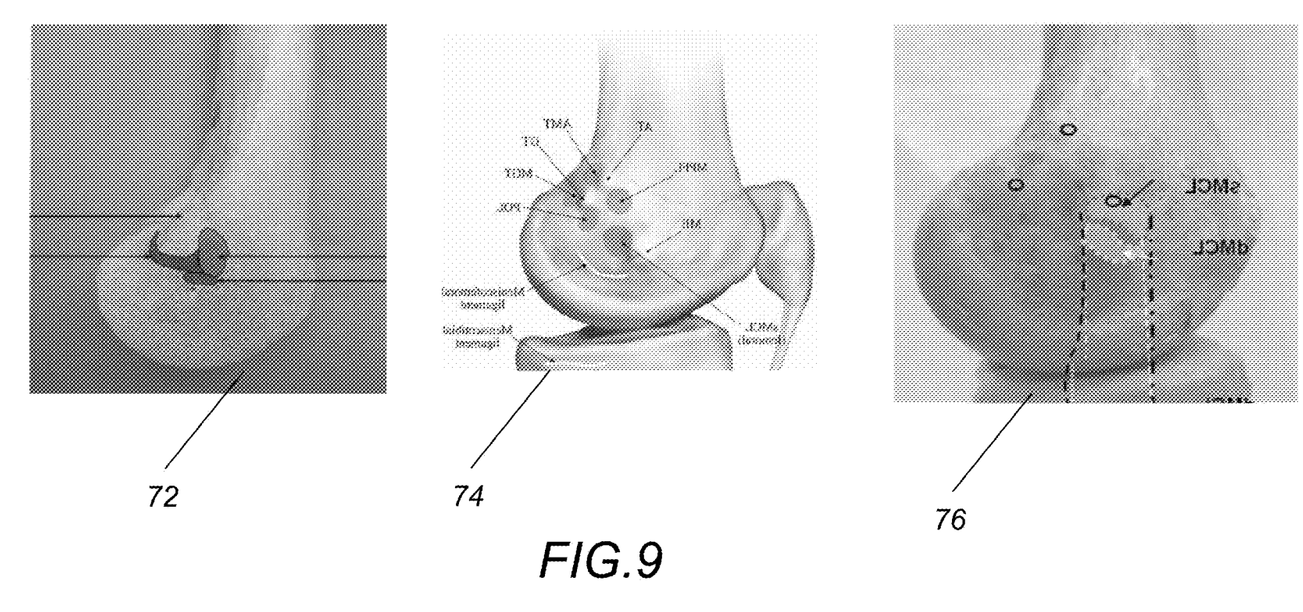
FIG. 9 shows MCL insertion sites according to Robinson 72, LaPrade 74, and Fang 76.
Figure 10A:
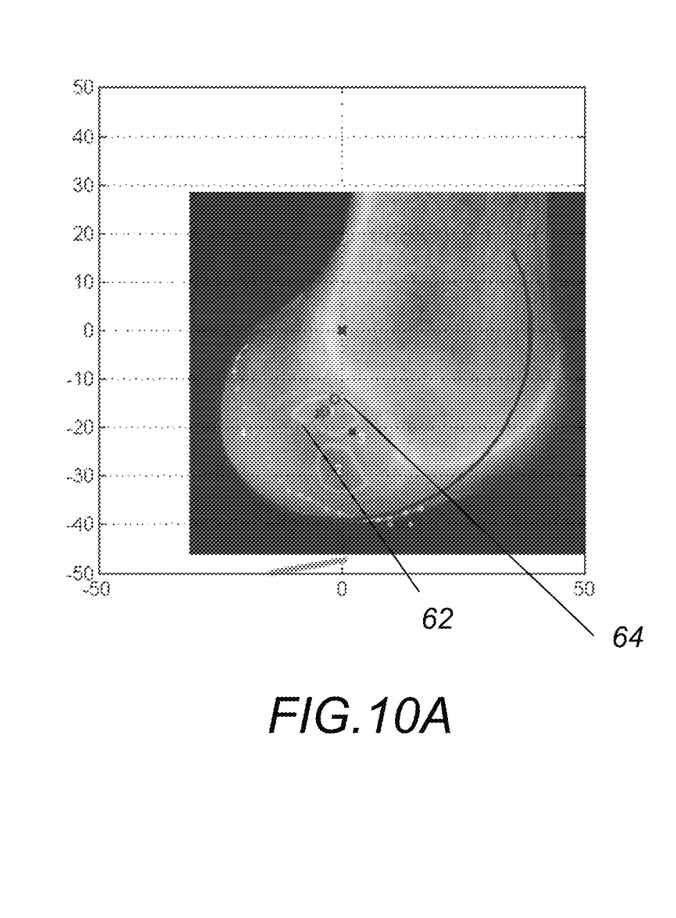
FIG. 10A shows the lateral collateral ligament (LCL) insertion sites 62 and the anterolateral ligament insertion (ALL) sites 64 as determined by the adaptive migration.
Figure 10B:
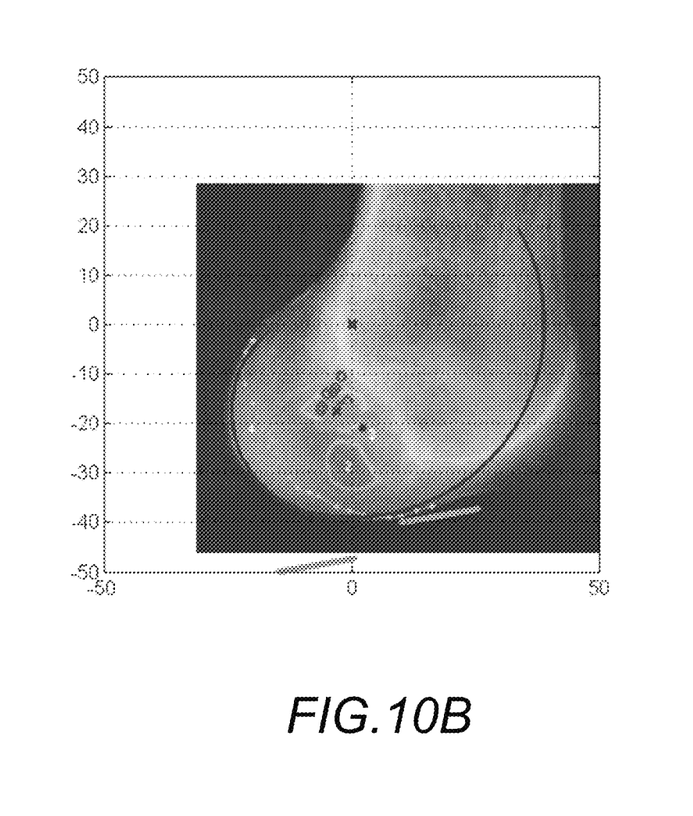
FIG. 10B shows an exploration of several of the variables which may be used to shape the adaptive migration responses to external influences such as anterior tibial translation under load and lateral condylar roll back under passive motion.

The calculated results are overlaid over photographs and artists drawings of the knee osseous surface, extracted from the literature. FIG. 9 depicts MCL insertion sites according to Robinson 72, LaPrade 74 and Fang 76. The representation of geometry shows great variation in the literature and none of the sources claims the images to be geometrically accurate. FIG. 10A shows the lateral collateral ligament (LCL) insertion sites 62 and the anterolateral ligament insertion (ALL) sites 64 as determined by adaptive migration. The two clusters of circles 62 represent the LCL under two conditions of anterior displacement 0 and 4 mm displacement while the circles 64 indicate the anterior lateral insertions. The LCL is well represented in the insertion area shown in this figure. The anterior lateral insertion differs from the literature reports in that it is slightly proximal to the LCL insertion rather than slightly distal. Nevertheless the ALL is said to insert at about the same place as the LCL which is the finding of the adaptive migration approach. FIG. 10B shows an exploration of several of the variables which may be used to shape the adaptive migration responses to external influences such as anterior tibial translation under load and lateral condylar roll back under passive motion.

Areas of Application
Knee Modeling and Research

Numerous researchers have developed knee models incorporating line element representations of the ligaments. This is an appealing approach for joint modeling to provide a tool to improve understanding and visualizing of the mechanics of the joint system. In general the approach requires defining the ligament insertion geometry and articular contact geometry based on measurements taken during dissection of the knee. Once the basic geometry is developed the computational model is further informed with material stiffness properties for the line element fibers. All that is then needed is an estimate of the condition of ligament strain at some reference pose. This is accomplished by providing a reference strain or reference length of the ligament fiber which defines the tension in the element at the chosen reference pose. However accomplishing an absolute measure of strain at a known pose presents a challenge, so various indirect approaches have been taken to estimate the reference pose strain condition. An optimization approach is frequently adopted which involves exercising the model through a prescribed kinematic path while determining the strain developed in each ligament element. The reference strain is then adjusted to seek a strain energy minimum throughout the prescribed kinematic path using an optimization search algorithm.

The deficiencies of this conventional approach are several. First, choice of insertion sites, although based on apparent geometry, no matter how accurate, is at best arbitrary. Insertion site choice might be based on a single point located at the centroid of the insertion foot print, or perhaps on multiple points on the margin of the foot print spanning the principle dimensions. But given that the model utilizes a simplified representation of the ligament elements, then constraining their insertion site to the geometry of the natural insertion site is not necessarily the best choice for the model insertion geometry. This fact is borne out by the results of the strain energy optimization approach which often leads to impossibly large strains at certain poses.

More recent models have finely partitioned the ligament material into a multitude of macro fibers to better represent the insertion geometry. But in all cases an attempt is made to model a continuous highly deformable material, which has its own complex behavior, with a finite series of elements of simple non interacting geometry. There is no convincing proof that such simple line elements may be best chosen within the confines of the foot print of the natural elements.

Choice of fiber insertion sites based on the geometry of the natural ligament footprint is compelling for reasons of geometric similarity; however, this is deceptive. We know that our finite fiber model is a rough approximation of the real complexity of the knee. The insertion sites that have evolved and developed for the natural system are not necessarily the best insertion sites choices for our simplified model. The adaptive migration approach borrows on a notion widely used in fluid modeling; that is the notion of similitude. Simple geometrical scaling fails for fluid modeling because many of the important properties of fluids do not scale linearly with dimension. In fluid modeling the concept of similitude is used to overcome this difficulty. Our goal with the adaptive migration approach is to establish a structural similitude between our simplified model and the natural system. We know that ligaments represented by a limited number of finite fibers will not behave exactly as natural ligaments composed of continuous material but we seek to find insertion sites that will best characterize the structural and mechanical properties of the natural system. To do so we utilize our adaptive migration approach to find insertion sites that best represent the mechanical function of the system based on some simple rules and assumptions. Our goal of course is to produce a model comprised of articular surface geometry and a finite number of ligament fibers that 'optimally' represents the mechanics and kinematics of the natural (or implanted) knee.

Computer Assisted Navigation in Surgery

There is an interest in the industry to develop scalable representations of the osseous and ligamentous geometry of the knee for the use in TKR planning and computer navigated surgery. Statistical approaches have been used with limited success. The adaptive migration concept provides a basis for ligament scaling around functional mechanical criteria rather than statistical methods. Coupled with other navigation and imaging techniques the adaptive migration concept adds value in promoting understanding of biomechanics and function.

TKR Design

If we have achieved structural similitude between our model and the natural knee then the task of evaluating a TKR design becomes almost trivial. We need simply substitute the TKR condylar surface geometry into the natural knee model and exercise the model through the desired kinematic and kinetic paths to evaluate performance. Furthermore we can reevaluate the insertion site geometry to determine the required changes to establish similitude with the TKR geometry in place.

Surgical Ligament Balancing

During total knee arthroplasty is frequently necessary to perform ligament balancing to achieve reasonable kinematic performance. Our methodology directly addresses the balancing problem. We can determine the optimum insertion sites based on the prosthetic geometry given particular distal insertion site information.

TKR Testing and Evaluation

Our direct application area is in the area of implant testing. In this area it is desirable to be able to test TKR hardware in an environment that simulates the structural properties of the healthy and diseased natural knee. Our Vivo control system has been developed to incorporate ligament insertion site information and ligament mechanical properties as will be output by the adaptive migration process. This data is then used by the Vivo controller to create a virtual environment in which to test TKR devices. The adaptive migration process enables us to easily create representations of various post-surgical ligament conditions representing the spectrum of surgical outcomes.

Patient Specific TKR

The adaptive migration concept also permits us to develop non-optimum models such as the effect of ligament contracture due to osseous pathologies. In fact this might be an excellent way to estimate the extent of contracture preoperatively given input from MRI or CT to quantify the degenerated osseous structure. The ability to mechanically represent patient pathologies will be particularly important in the area of patient specific implants.

Surgical Instruction and Education

Yet another area of application is for surgical and mechanical education. This concept rapidly and convincing demonstrates the interactions of the ligament structure and bony geometry of the joint. Three dimensional visualization adds a further element of clarity to the system.

Ligament Reconstruction Surgery

The adaptive migration concept has direct application to ligament reconstructive surgery as the ideal insertion sites for the replacement ligament material or graft can be determined based on the patient's joint geometry. Reconstruction of the ACL is one of the most frequent orthopedic procedures in the US today. MCL reconstruction is also quite frequent while PCL reconstruction is gaining frequency. In all of these cases the adaptive migration methodology lends insights into optimum location for replacing ligament material.

The adaptive migration concept is applicable to all of the joints of the human body and can also be used in veterinary reconstructive surgery applications.

In summary, adaptive ligament migration is compelling. These proof-of-concept results demonstrate that adaptive migration is an attractive approach for scaling ligament geometry to bony geometry. The required inputs are: 1) accurate geometry representing the contacting articular surfaces, 2) reasonable geometry representing the distal (tibial) insertion sites, 3) a passive kinematic path.

Several embodiments of the present invention have been described. Nevertheless, it will be understood that various modifications may be made without departing from the spirit and scope of the invention. Accordingly, other embodiments are within the scope of the following claims.

What is claimed is:

1. A system for providing feedback during ligament insertion in knee joint orthopedic surgeries comprising:
    an imaging device providing knee joint articular surface geometry data;
    a position measuring device providing distal ligament insertion sites;
    a strain measuring device providing ligament reference strain;
    a drive system providing a prescribed kinematic path for the knee joint;
    an adaptive migration application configured to receive inputs comprising said knee joint articular surface geometry data, said distal ligament insertion sites, said ligament reference strain and said prescribed kinematic path for the knee joint and to generate outputs comprising sets of isotonic, hypertonic and hypotonic points representing proximal insertion sites of a ligament fiber associated with prescribed distal ligament insertion sites;
    wherein the adaptive migration application generates said set of isotonic, hypertonic and hypotonic points so that the ligament fiber stretched between two isotonic points has minimal change in tension throughout a flexion arc.

2. The system of claim 1, wherein the knee joint articular surface geometry data are represented as two tangentially intersecting circular arcs.

3. The system of claim 1, wherein the adaptive migration application generates said set of isotonic, hypertonic and hypotonic points by iteratively adapting the distal ligament insertion sites based on an integral of a ligament tension vector over a flexion arc.

4. The system of claim 3, wherein said integral of the ligament tension vector trends towards a limit of zero with successive iterations of the adaptive migration application and wherein at said limit a distal ligament insertion site is determined that balances tensile and compressive strain over the flexion arc.

5. The system of claim 1, wherein the prescribed kinematic path for the knee joint comprises passive kinematics of the knee joint through a flexion arc.

6. The system of claim 1, wherein the prescribed kinematic path for the knee joint comprises one of flexion, internal rotation, anterior posterior displacement or medial lateral displacement.

7. The system of claim 1, wherein the prescribed kinematic path for the knee joint is applied while the knee joint is constrained in two degrees of freedom.

8. The system of claim 1, wherein the adaptive migration application further determines a cost function based on applied strain magnitude and direction of a strain induced tension in the ligament fiber.

9. The system of claim 8, wherein the adaptive migration application migrates the distal ligament insertion sites in a direction counterpoised to a direction of the induced tension in the ligament fiber throughout a flexion arc.

* * * * *